(12) United States Patent
Huotari et al.

(10) Patent No.: US 7,890,184 B2
(45) Date of Patent: Feb. 15, 2011

(54) CONDUCTOR JUNCTIONS FOR MEDICAL ELECTRICAL LEADS

(75) Inventors: Craig T. Huotari, Crystal, MN (US); Joseph F. Lessar, Coon Rapids, MN (US); Mark D. Breyen, Champlin, MN (US); Ryan Thomas Bauer, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 836 days.

(21) Appl. No.: 11/669,432

(22) Filed: Jan. 31, 2007

(65) Prior Publication Data

US 2008/0178449 A1 Jul. 31, 2008

(51) Int. Cl.
*A61N 1/05* (2006.01)
(52) U.S. Cl. ...................... 607/116; 607/119
(58) Field of Classification Search .............. 607/116, 607/117, 119, 122; 128/786
See application file for complete search history.

(56) References Cited

U.S. PATENT DOCUMENTS

| 3,769,984 | A | 11/1973 | Muench |
| 4,214,804 | A | 7/1980 | Little |
| 4,592,372 | A * | 6/1986 | Beranek ............... 607/119 |
| 5,700,082 | A | 12/1997 | Peng |
| 6,066,166 | A | 5/2000 | Bischoff et al. |
| 2004/0230268 | A1 | 11/2004 | Huff |
| 2005/0240252 | A1* | 10/2005 | Boser et al. ............. 607/116 |

FOREIGN PATENT DOCUMENTS

| DE | 202005020835 U1 | 9/2006 |
| EP | 0 292 596 A | 11/1988 |

OTHER PUBLICATIONS

International Search Report, PCT/US2008/052255, Jun. 6, 2008, 6 Pages.

\* cited by examiner

*Primary Examiner*—Carl H Layno
*Assistant Examiner*—Pamela M Bays
(74) *Attorney, Agent, or Firm*—Carol F. Barry

(57) ABSTRACT

A core component of a medical electrical lead extends within an inner conductive surface of a conductive ring such that an outer surface of the core holds a portion of a conductor against the inner conductive surface for electrical contact therewith. The outer surface of the core may be deformed by a compressive force of the conductor portion having been forced against the inner surface of the ring. Such a conductor junction may be formed by pushing the ring over the core to capture the conductor portion between the ring and the core and thereby displace a layer of insulation surrounding the conductor portion. The inner surface of the ring preferably has a diameter at one, or both terminal ends that is greater than a diameter of the inner surface between the ends.

26 Claims, 6 Drawing Sheets

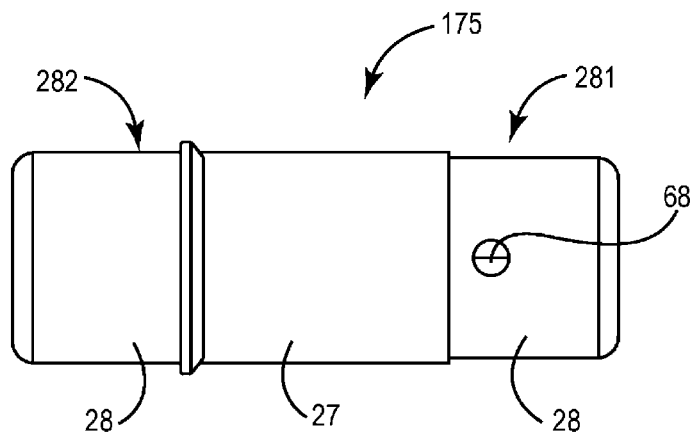
Fig. 6A
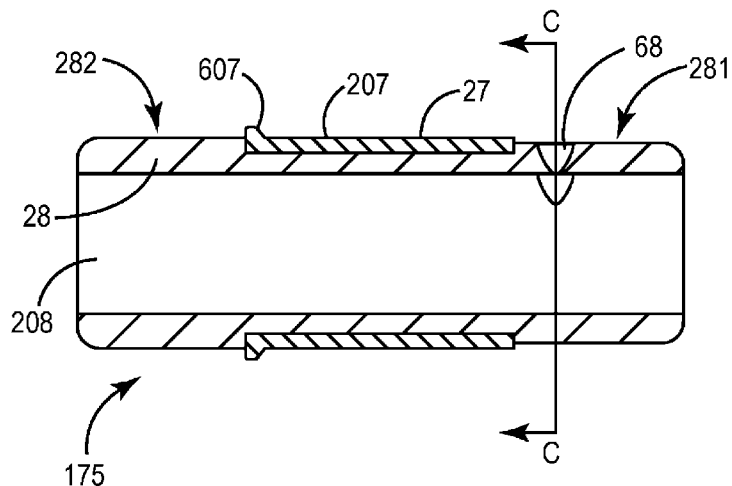 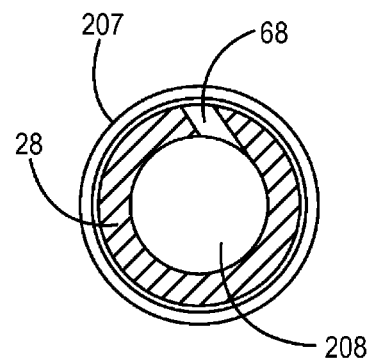
Fig. 6B  Fig. 6C

US 7,890,184 B2

CONDUCTOR JUNCTIONS FOR MEDICAL ELECTRICAL LEADS

TECHNICAL FIELD

The present invention pertains to medical electrical leads and more particularly to conductor junctions thereof.

BACKGROUND

A medical electrical lead typically includes one or more elongate conductors, each of which electrically couples an electrode of the lead to a corresponding connector contact of the lead. Each conductor includes a conductor wire surrounded by a layer of insulation to electrically isolate one wire from another and/or to isolate each wire from the operating environment of the lead, for example, within a body of a patient who receives therapy via the lead.

According to some lead designs known in the art, the insulating layer is formed directly over each conductor wire; lead conductor wires may be a cabled plurality of individual wire strands or one or more individual wire filars formed into a coil. In order to electrically couple a lead electrode to a lead connector contact, the insulating layer of the corresponding conductor must be removed from at least two portions of the corresponding wire, a first portion at a junction with the electrode, and a second portion at a junction with the contact. Each of these junctions should add a minimum of electrical resistance to the electrical circuit, which is formed by the electrode, conductor, and contact, and have an adequate strength to maintain good contact under operational loading conditions. Although many such conductor junctions are known in the art, there is still a need for improved conductor junctions which, in addition meeting the above criteria, can facilitate manufacturing efficiency of medical electrical leads.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

FIGS. 6A-C are a plan view, a longitudinal cross-section view, and a radial section view of a core component, according to some embodiments of the present invention.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

Figure 1:
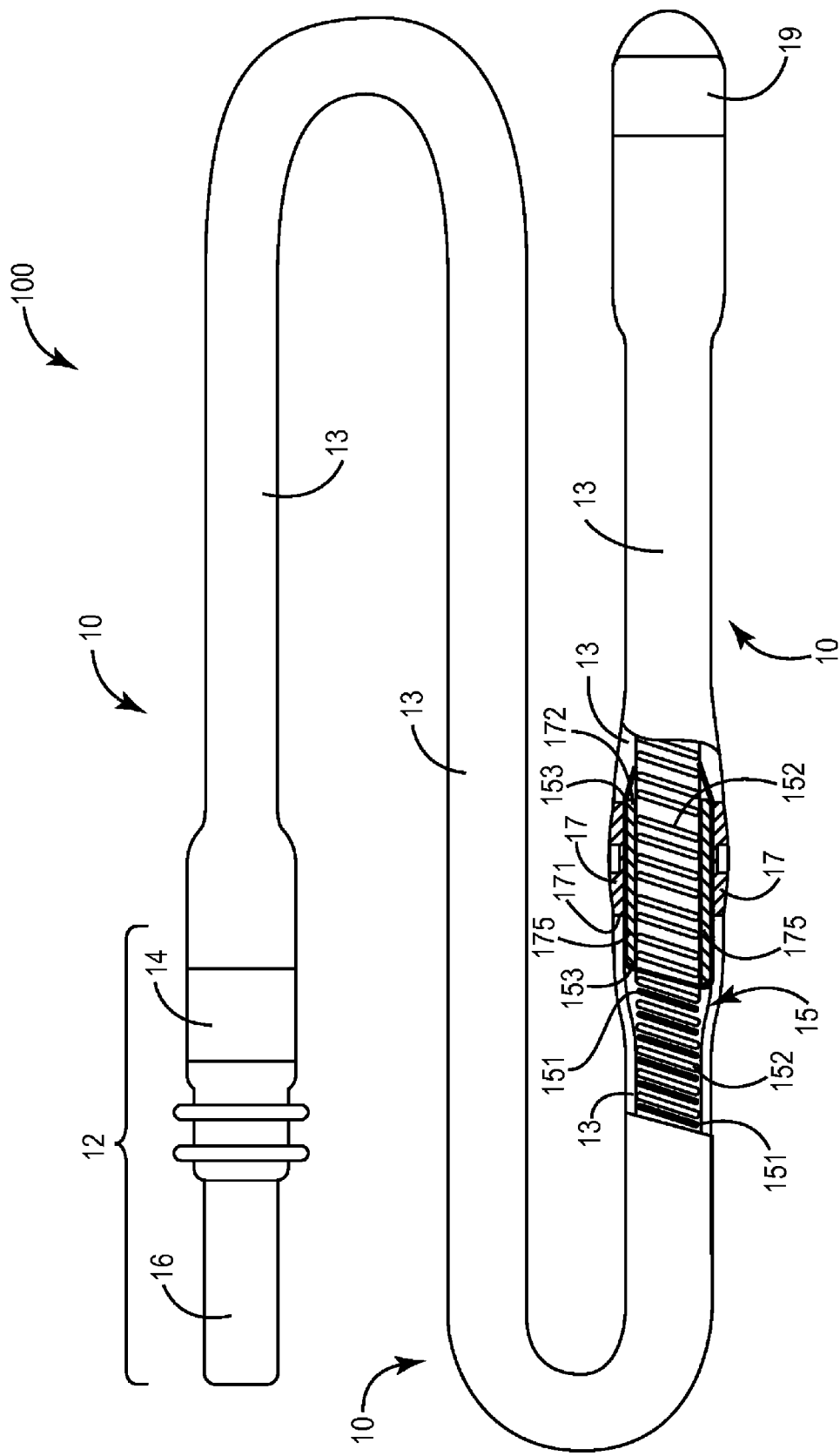
FIG. 1 is a plan view including a partial cut-away section of an exemplary medical electrical lead including a conductor junction, according to some embodiments of the present invention.

FIG. 1 is a plan view including a partial cut-away section of an exemplary medical electrical lead 100 including a conductor junction, according to some embodiments of the present invention. FIG. 1 illustrates lead 100 including an elongate lead body 10 to which a first, or proximal electrode 17 and a second, or distal electrode 19 are coupled; lead body 10 includes an elongate coil conductor 15 extending within an outer insulation tube 13, and is terminated, at a proximal end, by a connector 12, which includes a ring contact 14 and a terminal pin contact 16. According to the illustrated embodiment, a first conductor 151 of coil conductor 15 electrically couples one of ring contact 14 and pin contact 16, preferably ring contact 14, to proximal electrode 17, and a second conductor 152 of coil conductor 15, being electrically isolated from first conductor 151, electrically couples the other of ring 14 and pin 16, preferably pin 16, to distal electrode 19. Those skilled in the art will appreciate that lead 100 may be implanted within a body of a patient such that connector 12 is coupled to an implanted device, for example, a cardiac pacemaker, and electrodes 17, 19 are positioned for cardiac pacing and/or sensing. Although two conductors 151, 152, two electrodes 17, 19, and two corresponding connector contacts 14, 16 and are shown, the scope of the present invention is not limited leads having this or any particular number of conductors and electrodes.

FIG. 1 further illustrates first conductor 151 and second conductor 152 extending side-by-side, proximal to first electrode 17, to form coil 15, and illustrates electrode 17 in the form of a ring; in close proximity to a first or proximal end 171 of electrode ring 17, a portion 153 of first conductor 151 is shown leaving a helical path of coil 15 to extend within an inner diameter of electrode ring 17 in order to make a junction for electrical coupling therewith, while second conductor 152 remains in the helical path and extends distally to second electrode 19, for electrical coupling therewith. According to the illustrated embodiment, portion 153 of first conductor 151 extends between a core component 175 and electrode 17 to form a junction for electrical coupling of electrode 17 to a connector contact, for example, ring contact 14, via first conductor 151. A portion of the junction is shown in cross-section in FIG. 2B and will be described in greater detail below.

Figure 2A:
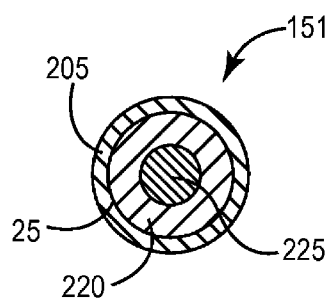
FIG. 2A is a cross-section view of a conductor included in the lead shown in FIG. 1, according to some embodiments of the present invention.

FIG. 2A is a cross-section view of first conductor 151. FIG. 2A illustrates first conductor 151 including a conductor wire or wire filar 25 surrounded by a layer of insulation 205, for example, a fluoropolymer or a polyimide, preferably, SI polyimide, which provides electrical isolation between first conductor 151 and second conductor 152 in the coiled configuration illustrated in FIG. 1. FIG. 2A further illustrates wire filar 25 formed by a conductive tube 220, for example, MP35N alloy, which is filled with a more conductive material 225, for example, silver. Second conductor 152 may, or may not, have a insulating layer and be a filled tube like first conductor 151. According to alternate embodiments, either, or both, of first and second conductors 151, 152 are formed from a cabled plurality of wire strands, for example silver-cored MP35N alloy strands. It will be appreciated that, in order to provide effective electrical isolation between first and second conductors 151, 152, insulation layer 205 should completely surround a circumference of conductor wire 25; yet, in order to form the junction with electrode 17 for electrical coupling, insulation layer 205 needs to be displaced from at least a portion of the circumference of wire 25 at the junction. According to preferred embodiments of the present invention, displacing insulation layer 205 and forming the junction between first conductor portion 153 and electrode 17 is accomplished in a single manufacturing step; details of such a manufacturing method will be described below, in conjunction with FIGS. 3 and 4A-D.

Figure 2B:
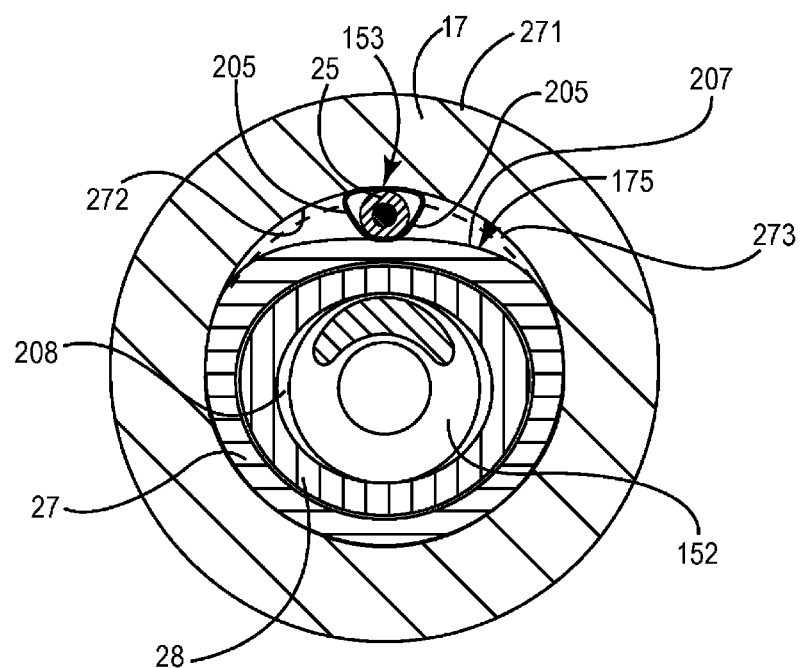
FIG. 2B is a cross-section view of a conductor junction, for example, the junction shown in FIG. 1, according to some embodiments of the present invention.

FIG. 2B is a cross-section view, in proximity to first end 171 of electrode ring 17, of the junction between first conductor portion 153 and electrode ring 17, according to some embodiments of the present invention. FIG. 2B illustrates core component 175 including an outer surface 207, which holds conductor portion 153 against an inner conductive surface 272 of electrode ring 17 in an interference press fit, and illustrates layer of insulation 205 that is displaced from an interface between inner surface 272 and conductor portion 153 so that wire filar 25 may make electrical contact with inner conductive surface 272. With reference to FIG. 2B it may be appreciated that core component 175 has been deformed by a compressive force of conductor portion 153 having been forced against inner conductive surface 272 of electrode ring 17 in a press fit process; dashed lines in FIG. 2B indicate a profile of core 175 prior to forming the junction. According to preferred embodiments of the present invention, forming the junction shown in FIG. 2B may be accomplished according to press fit methods described in FIGS. 3 and 4A-D. It should be noted that, although the junction and methods of manufacture are described in the context of FIG. 1 for electrode 17, such a conductor junction, formed according to the methods described below, may be incorporated for any ring component of a lead, for example, ring contact 14 and distal electrode 19 of lead 100. Furthermore, the scope of the present invention is not limited to coiled conductors, although preferred embodiments described herein employ coiled conductors.

Figure 3:
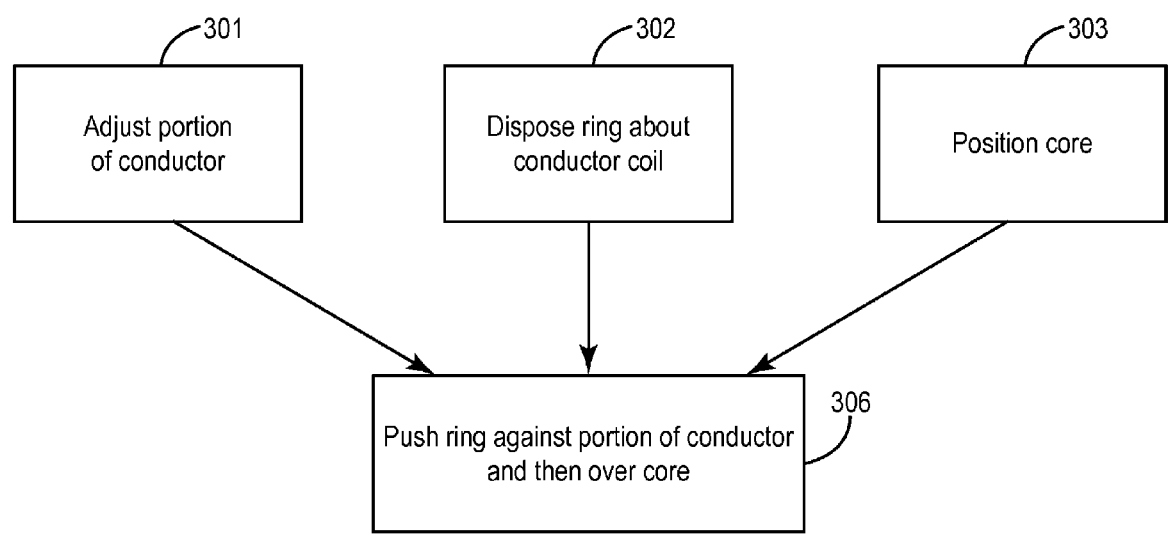
FIG. 3 is a flow chart outlining some methods of the present invention.
Figure 4A:
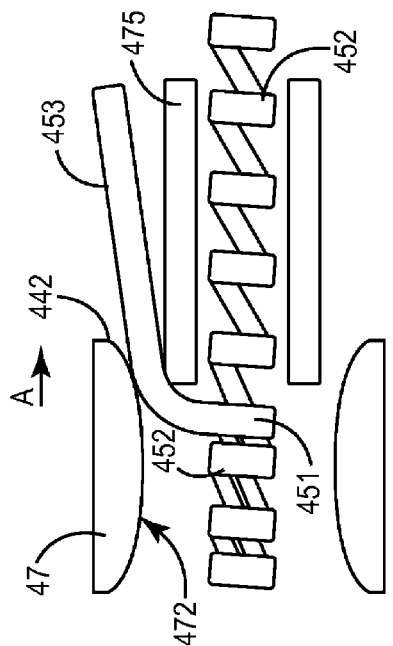
FIGS. 4A-D are assembly process schematics corresponding to a method outlined by the flow chart of FIG. 3.
Figure 4B:
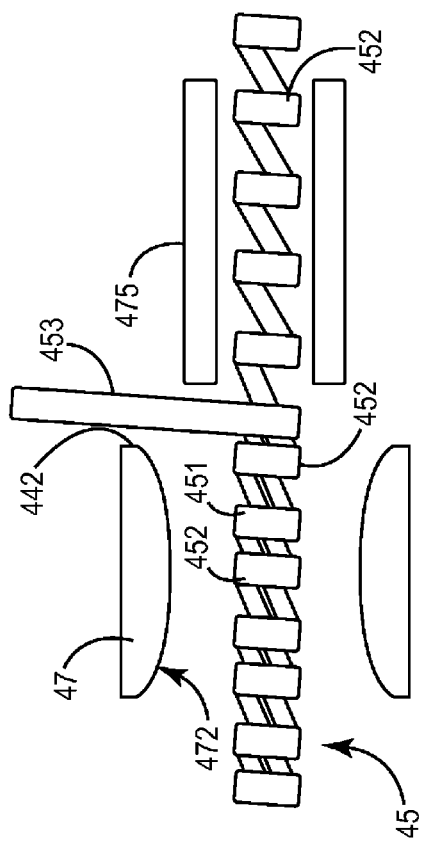
Figure 4C:
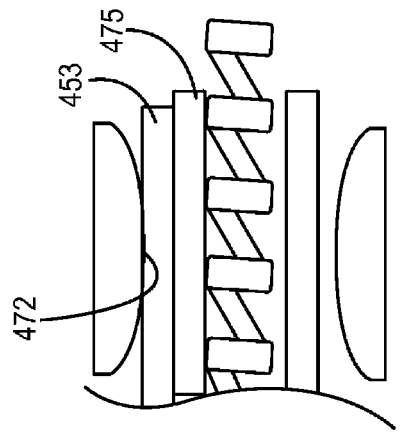
Figure 4D:
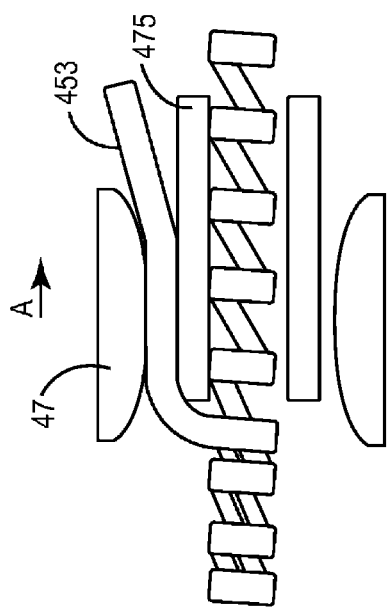

FIG. 3 is a flow chart outlining some methods of the present invention; and FIGS. 4A-D are assembly process schematics corresponding to a method outlined by the FIG. 3 flow chart. FIG. 3 shows three initial method steps 301, 302 and 303, which may be performed in any order with respect to one another. FIG. 4A illustrates a terminal portion 453 of a first conductor 451 (comparable to first conductor portion 153 of FIGS. 1 and 2B) of a conductor coil 45 having been adjusted, or bent, per step 301, such that terminal portion 453 is approximately straightened to extend out from a helical path of coil 45, in which path a second conductor 452 of coil 45 continues beyond first conductor 451. FIG. 4A further illustrates a ring component 47 (comparable to electrode ring 17) having been disposed about coil 45, per step 302, on a first side of conductor terminal portion 453, and a core component 475 (comparable to core component 175) having been positioned, per step 303, on a second side of terminal portion 453. Although FIGS. 4A-D illustrate core component 475 being disposed about second conductor 452 of coil 45, some embodiments of the present invention need not include second conductor 452. Once ring 47, conductor terminal portion 453 and core 475 are set up, as illustrated in FIG. 4A, step 306 of FIG. 3 may be accomplished, as illustrated in FIGS. 4B-D.

FIG. 4B illustrates a leading edge 442 of ring 47 having been pushed, per arrow A, against conductor terminal portion 453, to bend terminal portion 453 toward core 475. In FIG. 4B an inner conductive surface 472 is just starting to ride over terminal portion 453 and core 475. According to preferred embodiments of the present invention, first conductor 451 includes an insulating layer, for example, layer 205 of first conductor 151 illustrated in FIG. 2A, which extends over conductor terminal portion 453, and the action of ring inner surface 472, riding over portion 453, displaces the insulation layer without significantly deforming portion 453, for example, to the point of compromising a tensile strength of second conductor 451. FIG. 4C illustrates ring 47 having been pushed further, per arrow A, over conductor terminal portion 453 and core 475, to capture portion 453 between ring 47 and core 475; and FIG. 4D illustrates the junction completed wherein core 475 holds conductor terminal portion 453 against ring inner conductive surface 472 to form an electrical coupling therebetween, for example, as is illustrated in FIG. 2B.

Figure 5A:
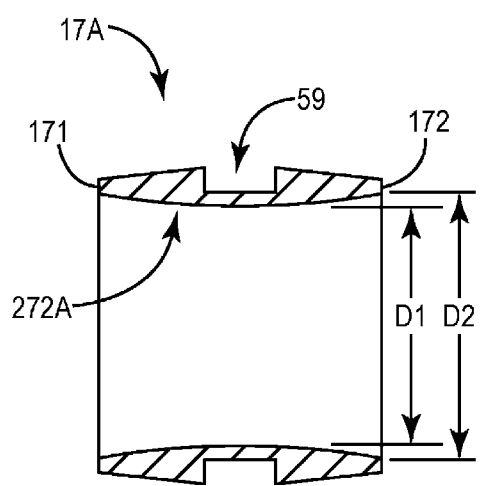
FIGS. 5A-B are longitudinal cross-section views of alternate electrode rings, according to some embodiments of the present invention.
Figure 5B:
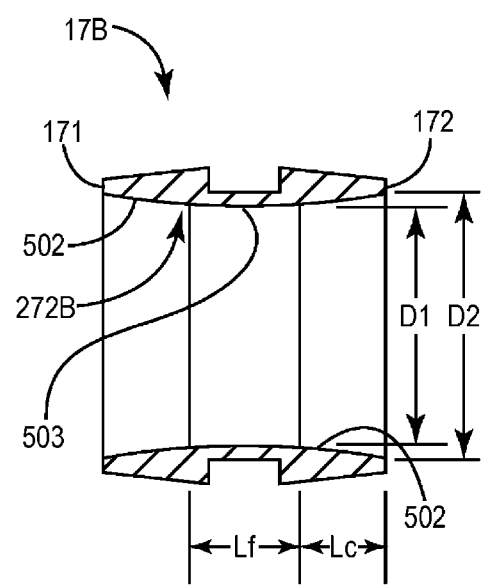

With reference to FIGS. 4A-D, it may be appreciated that an enlarged inner diameter of ring 47, in proximity to leading edge 442, allows ring leading edge 442 to push conductor terminal portion 453 toward core 475 and to start riding over terminal portion 453 and core 475 without significantly damaging second conductor 451. FIGS. 5A-B are longitudinal cross-section views of alternate embodiments 17A,B of electrode ring 17. According to preferred embodiments of the present invention, inner conductive surfaces 272A,B include curved profiles joining a first inner diameter D1 to a second, enlarged inner diameter D2 in proximity to a second end 172 of ring 17A,B (corresponding to leading edge 442 of FIGS. 4A-D). FIG. 5A illustrates inner surface 272A having a parabolic profile extending from second diameter D2 at first end 171 to second diameter D2 second end 172, wherein first inner diameter D1 is located at an approximate center point along a length of ring 17A. FIG. 5B illustrates inner surface 272B including first portions 502 having curved profiles extending from first inner diameter D1 to second inner diameter D2 at either end 171, 172, and a second portion 503 having a relatively flat profile defining first inner diameter D1. FIG. 5B further illustrates the curved profile of at least one of first portions 502 extending over a length Lc; according to preferred embodiments, Lc may be within a range from approximately 22% to approximately 50% of an overall length Lo of ring 17B. Although the presence of enlarged, or second diameter D2 at either end 171, 172 is preferred for simplicity in manufacturing, it should be appreciated that enlarged inner diameter D2 need only be present at the end corresponding to the leading edge of the press fit method, i.e. edge 442 of FIGS. 4A-D, which, with reference to FIGS. 1 and 5A-B, is second end 172.

According to preferred embodiments of the present invention, a clearance between ring first inner diameter D1 and an outer diameter of core component 175 is less than approximately 0.001 inch, a clearance between second inner diameter D2 and the outer diameter of core component 175 is at least approximately 0.006 inch, and a diameter of first conductor 151, extending to terminal end of first conductor portion 153, is approximately 0.005 inch, which diameter includes twice a thickness of insulation layer 205, which may be approximately 0.0005 inch. If overall ring length Lo is approximately 0.60 inch, a radius of the curved profiles of ring inner surfaces 272A, B may be within a range from approximately 0.01 inch to approximately 0.185 inch, increasing with increasing length Lc.

With reference back to FIG. 2B, which is a cross-section of the conductor joint in proximity to ring first end 171, it may be appreciated that enlarged diameter D2, initially riding over first conductor portion 153/453 and core 175/475 (FIG. 4B), has prevented significant damage to wire filar 25 during the press fit method, while ring first diameter D1 riding over conductor portion 153/453 and core 175/475 (FIG. 4C), in an interference fit, has effectively displaced insulation layer 205 from about the circumference of wire filar 25, for electrical coupling, and deformed outer surface 207 of core 175. It may also be appreciated that an elastic deformation of core 175 shown in FIG. 2B further facilitates a press fit junction in which wire filar 25 is not significantly damaged; there may also be a relatively small amount of local deformation along ring inner surface 272 adjacent to first conductor portion 153. According to an exemplary embodiment of the present invention, outer surface 207 of core component 175 is part of a conductive ring 27 formed from titanium or a titanium alloy (i.e. Ti64Al4, CP Ti grade 2) and having an inner diameter of approximately 0.042 inch and an outer diameter of approximately 0.050 inch; electrode ring 17 is formed of a platinum alloy (i.e. 90/10 platinum/iridium) and has a maximum outer diameter of approximately 0.067 inch, a minimum outer diameter, at either end 171, 172 of approximately 0.062 inch, a first inner diameter D1 of approximately 0.051 inch and a second inner diameter D2 of approximately 0.056 inch; and first conductor portion 153 has the dimensions defined above.

FIG. 2B further illustrates core component 175 including a non-conductive wall 28 extending within conductive ring 27 of core 175 to electrically isolate ring 27 from second conductor 152. Non-conductive wall 28 may further extend longitudinally from one or both ends of ring 27 as is illustrated in FIGS. 6A-C. FIGS. 6A-C are a plan view, a longitudinal cross-section view, and a radial section view, through section line C-C, of core 175, according to some embodiments of the present invention. FIGS. 6A-B illustrate ring 27 being mounted on non-conductive wall 28 between a first extension 281 of wall 28 and a second extension 282 of wall. According to an exemplary embodiment, core 175 is insert injection molded, wherein wall 28 is formed from a polyurethane having a durometer of approximately 75D. With reference back to FIG. 1, it may be appreciated that first and second extension 281, 282 provide surfaces for joining core 175 to outer insulation tubing 13, which may also be formed from a polyurethane, for example, having a durometer of approximately 55D. It should be noted that, alternate embodiments of the present invention may employ completely non-conductive cores, since outer surface 207 of core 175 need not be conductive for electrical coupling between conductor portion 153 and inner conductive surface 272 of ring 17.

FIGS. 6A-C further illustrate conductive ring 27 of core 175 including a shoulder 607, and first extension 281 of non-conductive wall 28 of core 175 including a slot 68 formed therethrough to create a passageway through which first conductor portion 153 may extend. According to the illustrated embodiment, shoulder 607 forms a stop for second end 172 of electrode ring 17 that may be useful in an automated press fit process to control the travel of ring 17 being pushed by a fixture, which may be driven by a pneumatic piston.

In the foregoing detailed description, the invention has been described with reference to specific embodiments. However, it may be appreciated that various modifications and changes can be made without departing from the scope of the invention as set forth in the appended claims.

We claim:
1. A medical electrical lead, comprising:
an elongate conductor including a first portion, a second portion and a layer of insulation; the second portion extending from the first portion, and the layer of insulation completely surrounding a circumference of the first portion and partially surrounding a circumference of the second portion;
a conductive ring including a first terminal end, a second terminal end, opposite the first terminal end, an external conductive surface, an inner conductive surface having a first inner diameter and a second inner diameter; the first terminal end being disposed adjacent to the first portion of the conductor, the inner conductive surface extending around the second portion of the conductor and making electrical contact therewith, and the second inner diameter being disposed at the second terminal end and being greater than the first inner diameter; and
a core component extending within the inner surface of the ring and including an outer surface; the outer surface of the core holding the second portion of the conductor against the inner conductive surface of the ring for the electrical contact, and the outer surface of the core being deformed by a compressive force of the second portion of the conductor forced against the core by the first inner diameter of inner conductive surface of the ring.

2. The lead of claim 1, wherein the first portion of the conductor is coiled.

3. The lead of claim 1, wherein the second portion of the conductor is approximately straight.

4. The lead of claim 1, wherein the layer of insulation is displaced by the inner conductive surface of the ring to partially surround the circumference of the second portion of the conductor.

5. The lead of claim 1, wherein the external conductive surface of the ring comprises an electrode.

6. The lead of claim 1, wherein the external conductive surface of the ring comprises a connector contact.

7. The lead of claim 1, wherein a portion of the inner conductive surface of the ring has a curved profile joining the first inner diameter to the second inner diameter.

8. The lead of claim 7, wherein the curved profile comprises a length greater than approximately 22% of the overall length of the ring.

9. The lead of claim 7, wherein the curved profile comprises a length greater than approximately 35% of the overall length of the ring.

10. The lead of claim 1, wherein the second inner diameter is also disposed at the first terminal end of the ring.

11. The lead of claim 10, wherein the inner conductive surface of the ring has a parabolic profile extending from the first terminal end to the second terminal end.

12. The lead of claim 1, wherein
a clearance between a diameter of the outer surface of the core and the second inner diameter of the inner conductive surface of the ring is greater than a diameter of the second portion of the conductor.

13. The lead of claim 12, wherein the diameter of the second portion of the conductor is approximately 0.005 inch and the clearance between the diameter of the outer surface of the core and the second inner diameter of the inner conductive surface of the ring is approximately 0.006 inch.

14. The lead of claim 1, wherein the outer surface of the core component is conductive.

15. The lead of claim 1, wherein the outer surface of the core component is nonconductive.

16. The lead of claim 1, wherein the outer surface of the core component is conductive, and the core component further includes a nonconductive wall extending longitudinally from the conductive surface toward the first portion of the conductor.

17. The lead of claim 16, wherein the nonconductive wall includes a slot through which the second portion of the conductor passes.

18. The lead of claim 1, wherein the core component further includes a shoulder in close proximity to the second terminal end of the ring.

19. The lead of claim 1, further comprising another elongate conductor extending alongside the first portion of the elongate conductor and beyond the first portion through a lumen of the core component and beyond the second terminal end of the ring.

20. A medical electrical lead comprising:
an elongate lead body;
an elongate conductor extending through the lead body, wherein the elongate conductor comprises a proximal end and a distal end, conductive material extending from the proximal end to the distal end, and insulation surrounding the conductive material to electrically isolate the conductive material;
a core component extending along only a portion of the lead body, wherein a terminal portion of the elongate conductor contacts an outer surface of the core component; and
a conductive ring located over the core component, wherein the conductive ring comprises an external surface and an inner surface, wherein the terminal portion of the elongate conductor is located and compressed between the inner surface of the conductive ring and the outer surface of the core component, and wherein the conductive ring electrically couples to the conductive material in the terminal portion of the elongate conductor, wherein the conductive ring defines a lumen extending from a first end to a second end, wherein the lumen defines a first inner diameter and a second inner diameter, wherein the second inner diameter is greater than the first inner diameter, and further wherein the lumen comprises the second inner diameter at the first end of the conductive ring.

21. The lead of claim 20, wherein the conductive ring electrically couples to the conductive material of the elongate conductor where at least a portion of the insulation on the terminal portion of the elongate conductor is displaced from the conductive material of the elongate conductor between the inner surface of the conductive ring and the outer surface of the core component.

22. The lead of claim 20, wherein the conductive ring defines a lumen extending from a first end to a second end, wherein the lumen defines a first inner diameter and a second inner diameter, wherein the second inner diameter is greater than the first inner diameter, and further wherein the lumen comprises the second inner diameter at the first end and the second end of the conductive ring, and further wherein the lumen comprises the first diameter between the first end and the second end.

23. The lead of claim 20, wherein the conductive ring defines a lumen extending from a first end to a second end, wherein the lumen defines a first inner diameter and a second inner diameter, wherein the second inner diameter is greater than the first inner diameter, and wherein the lumen comprises the second inner diameter at the first end and the second end of the conductive ring and the first diameter between the first end and the second end, and further wherein the inner surface of the conductive ring defines a curved profile between the larger second diameter at the first end and the second end and the smaller first diameter located between the first end and the second end.

24. The lead of claim 20, wherein a clearance between a diameter of the outer surface of the core and the second inner diameter of the conductive ring is greater than a diameter of the terminal portion of the elongate conductor.

25. The lead of claim 20, wherein at least a portion of the outer surface of the core component is compressively deformed by the terminal portion of the elongate conductor and the inner surface of the conductive ring.

26. The lead of claim 20, wherein the core component comprises a passageway formed through a wall that defines an inner lumen and the outer surface of the core component, wherein the passageway extends between the inner lumen and the outer surface of the core component, and further wherein the elongate conductor extends through the passageway.

* * * * *

UNITED STATES PATENT AND TRADEMARK OFFICE
CERTIFICATE OF CORRECTION

| | | |
|---|---|---|
| PATENT NO. | : 7,890,184 B2 | Page 1 of 1 |
| APPLICATION NO. | : 11/669432 | |
| DATED | : February 15, 2011 | |
| INVENTOR(S) | : Craig T. Huotari et al. | |

It is certified that error appears in the above-identified patent and that said Letters Patent is hereby corrected as shown below:

Col. 5, line 16, delete "(ie. Ti64A14, CP Ti grade 2) and having an inner diameter of" and insert in place thereof -- (ie. Ti64A14, CP Ti grade 2) and having an inner diameter of --;

Signed and Sealed this
Fourteenth Day of February, 2012

David J. Kappos
*Director of the United States Patent and Trademark Office*